US00PP23458P3

(12) United States Plant Patent
Maillard et al.

(10) Patent No.: US PP23,458 P3
(45) Date of Patent: Mar. 12, 2013

(54) NECTARINE TREE NAMED 'NECTARBONDANT'

(50) Latin Name: ***Prunus persica* L. Batsch var. *nucipersica***
Varietal Denomination: NECTARBONDANT

(75) Inventors: Arsene Maillard, Elne (FR); Laurence Maillard, Elne (FR)

(73) Assignee: Agro Selections Fruits, Elne (FR)

( * ) Notice: Subject to any disclaimer, the term of this patent is extended or adjusted under 35 U.S.C. 154(b) by 0 days.

(21) Appl. No.: 13/064,019

(22) Filed: Mar. 2, 2011

(65) Prior Publication Data

US 2011/0219482 P1 Sep. 8, 2011

(51) Int. Cl.
*A01H 5/00* (2006.01)

(52) U.S. Cl. ..... Plt./188

(58) Field of Classification Search ..... Plt./188
See application file for complete search history.

*Primary Examiner* — Kent L Bell

(74) *Attorney, Agent, or Firm* — Westerman, Hattori, Daniels & Adrian, LLP

(57) ABSTRACT

A new and distinct variety of white nectarine tree, denominated 'NECTARBONDANT', has a large fruit of very long shelf life without alteration after harvesting, a semi-sweet white flesh of high eating quality and an attractive homogenous bright red skin color. The tree is of large size and is vigorous. Fruit can be consumed crunchy or at maturity.

3 Drawing Sheets

Latin name of the genus and species of the plant claimed: *Prunus persica* L. Batsch var. *nucipersica*.

Variety denomination: 'NECTARBONDANT'.

This application claims priority of Community plant variety right No. 2010/0485 filed on Mar. 2, 2010 which is hereby incorporated by reference in its entirety.

BACKGROUND OF THE NEW VARIETY

The present invention relates to a new and distinct variety of white nectarine tree, *Prunus persica* L. Batsch var. *nucipersica*, which has been given the variety denomination 'NECTARBONDANT'. This new tree produces fruit with a long shelf life without alteration both on the tree after growth completion and after harvesting, large fruit with very good eating quality, fresh fruit for fresh market in late August in the Pyrénées-Orientales department, France. Contrast is made to 'NECTAREXQUISE' (U.S. Plant Pat. No. 19,377) and 'NECTARLIGHT' (U.S. Plant Pat. No. 21,155), standard varieties, for reliable description. 'NECTARBONDANT' is a promising candidate for commercial success in that it has a semi-early to semi-late period of flowering, fruit with very long shelf life without alteration after harvesting, and so a very durable fruit.

ORIGIN OF THE VARIETY

'NECTARBONDANT' nectarine tree originated in a cultivated area of the south of France, in the Pyrénées-Orientales department, where it was tested. The male parent is 'NECTARMAGIE' (U.S. Plant Pat. No. 17,579), very productive white nectarine tree with very attractive fruit and the female parent is 'MAILLARDUCHESSE' (non-patented) a very productive white nectarine tree with a balanced flavor. 'NECTARMAGIE' (U.S. Plant Pat. No. 17,579) results from an open pollinated cross of 'MAILLARMAGIE' (MAGIQUE®) white nectarine tree that was used as the seed parent. As 'MAILLARMAGIE' (MAGIQUE®) nectarine tree has non-showy (campanulate) flowers, flowers blooming occur before pollen maturity. Cross-pollination with varieties in the vicinity of the mother-tree should have occurred. Pollen parent is unknown. It blooms in early March in South of France, more particularly one day after 'MAILLARMAGIE' (MAGIQUE®) variety, between March 3$^{rd}$ and March 15$^{th}$. The first fruit of 'NECTARMAGIE' (U.S. Plant Pat. No. 17,579) nectarine tree ripens in July, more particularly about 3 to 4 days before the first fruit of 'MAILLARMAGIE' (MAGIQUE®) variety, between July 3$^{rd}$ and July 13$^{th}$. It was obtained by hybridizing and propagated by grafting. 'MAILLARDUCHESSE' (non-patented) is a white nectarine tree with a period of maturity beginning on September 8$^{th}$. 'NECTARBONDANT' variety was obtained by hybridizing and propagated by grafting in Elne, Pyrénées-Orientales department, France. 'NECTARBONDANT' variety has been determined to have unique tree and fruit characteristics making it worthy for commercial fresh fruit production. There are no known effects of this standard rootstock on this scion cultivar. Asexually propagated plants remained true to the original tree and all characteristics of the tree and the fruit were transmitted.

We reproduced the plant of the 'NECTARBONDANT' variety asexually in Elne, Pyrénées-Orientales department, France. More particularly, the plant of the 'NECTARBONDANT' variety was reproduced by grafting.

SUMMARY OF THE VARIETY

The new and distinct variety of white nectarine tree 'NECTARBONDANT' blooms in late February near Elne in the Pyrénées-Orientales department, France. More particularly, it blooms at the same time as 'NECTAREXQUISE' (U.S. Plant Pat. No. 19,377). The blooming period is considered medium. The first fruit of 'NECTARBONDANT' ripens in late August, around 5 days after the first fruit of 'NECTAREXQUISE' (U.S. Plant Pat. No. 19,377) variety. More particularly, it approximately ripens between the 15$^{th}$ and the 22$^{nd}$ of August. The fruit of 'NECTARBONDANT' is very attractive with less lenticels, with a rounder shape, more beautiful and more homogenous, and its blush color is of a dark red on 60% of the fruit on a bright pink red ground. In comparison with 'NECTARLIGHT' (U.S. Plant Pat. No. 21,155) the blooming begins at the same period of the year and the first fruit ripens approximately at the same time. The fruit is very attractive and more colored than the fruits of 'NECTARLIGHT' (U.S. Plant Pat. No. 21,155).

DESCRIPTION OF THE DRAWINGS

In the accompanying pictures, which are as nearly true as it is reasonably possible to make in a color illustration of this type.

Figure 1:
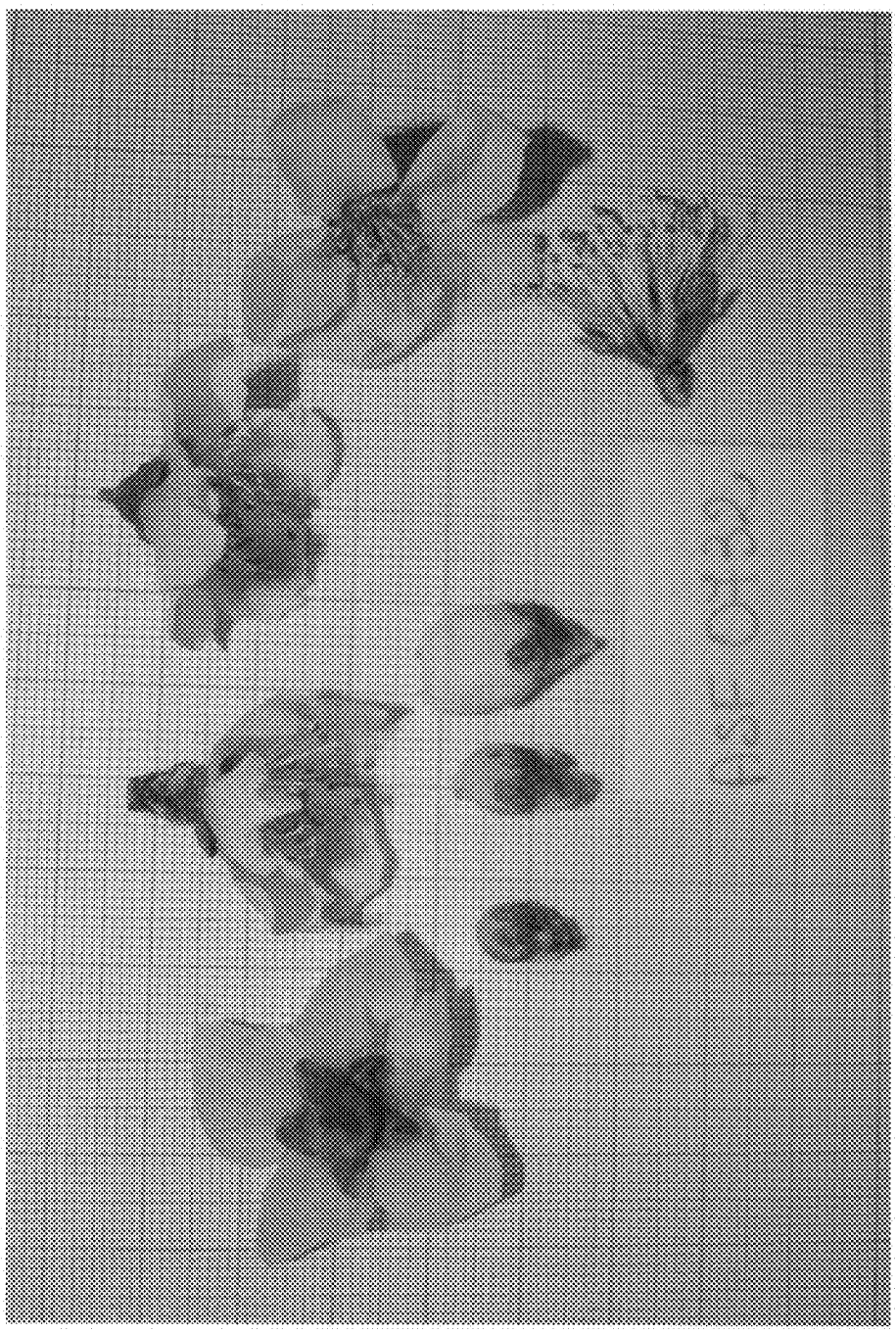
FIG. 1 is a color photograph which depicts the flower buds at different development stages, and the reverse and side view of the flower and the reproductive organs with petals removed, of the new variety.
Figure 2:
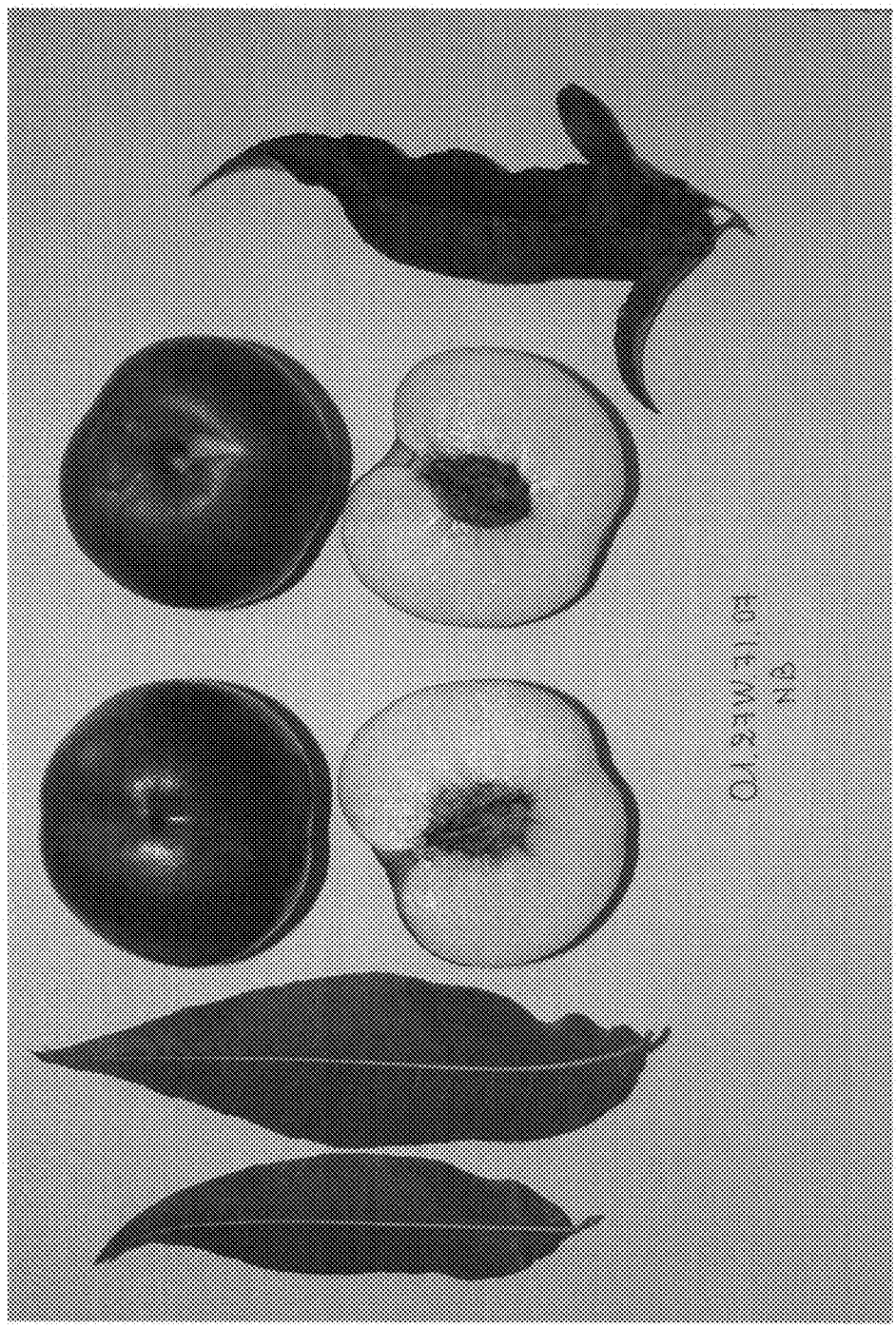
FIG. 2 is a color photograph which shows three typical specimens of the fruit, one having been cut in half with the pit being left in one of the halves for depicting fruit flesh, pit cavity, stone and leaves of the new variety.
Figure 3:
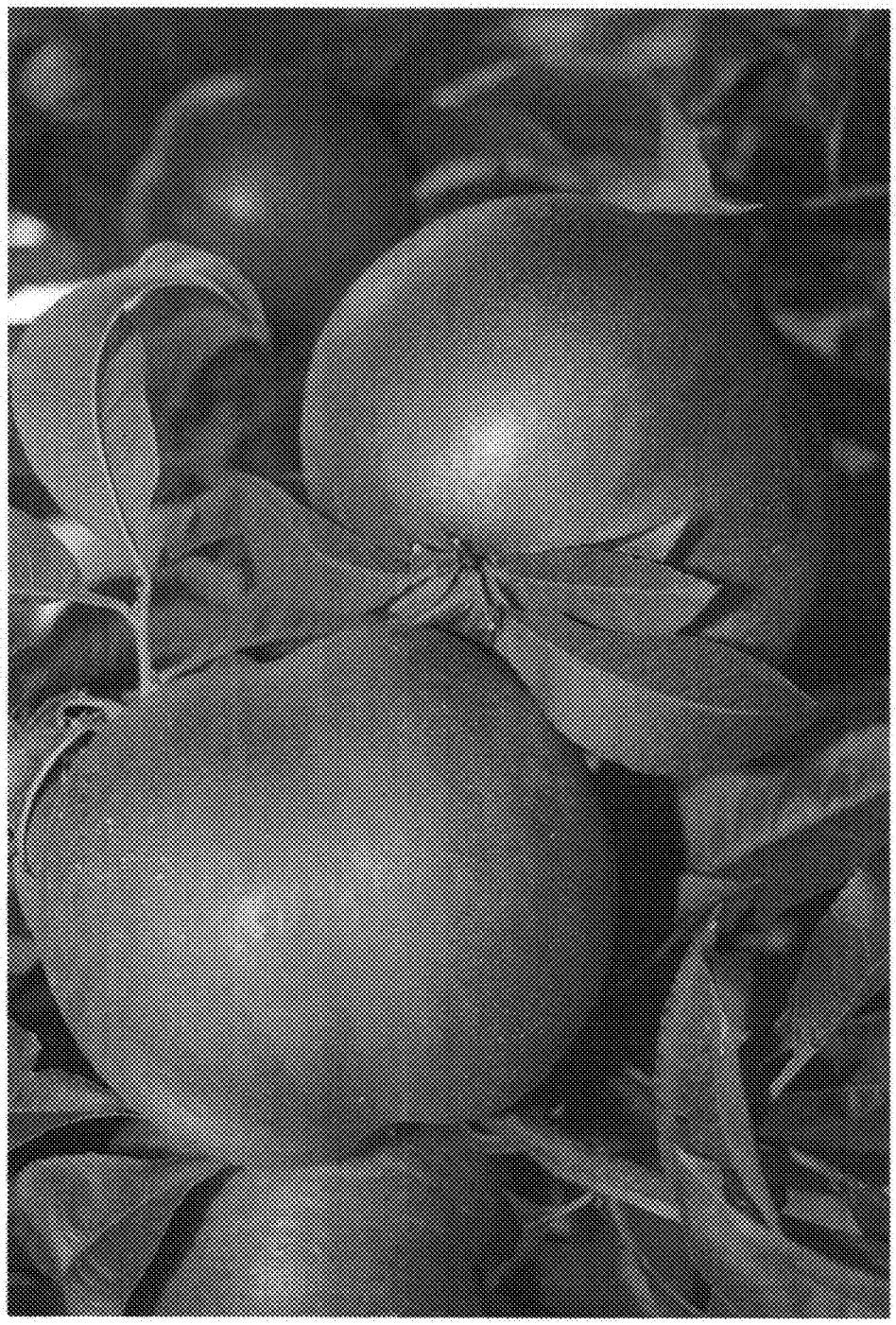
FIG. 3 is a color photograph that shows a close view of typical fruits of the new variety 'NECTARBONDANT' at ripening time.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruit by 'NECTARBONDANT' is high, due to fruit very long shelf life without alteration after harvesting.

Trees are vigorous and large stature half-standing in a semi-spread to a semi-upright aspect. The flowering shoot is present excluding brushwood side away from sun. Flowering begins semi-early to semi-late in springtime. The type of flower is showy, with medium petal size. Petals are medium pink to dark pink. Leaf glands are present and reniform. Time of maturity for consumption is considered semi-late. The fruit flesh is white with a slight red pigmentation into the stone cavity and also star-shaped around the stone cavity on about 7 millimeters. Fruit skin is very thick, of bright red color on a pink red ground. The stone is clingstone, of medium to large size and the flesh is very adherent. Fruit taste is semi-sweet.

Compared to 'NECTAREXQUISE' (U.S. Plant Pat. No. 19,377) variety presentation is higher with less lenticels.

Compared to 'NECTARLIGHT' (U.S. Plant Pat. No. 21,155) variety, the productivity is higher and the presentation and color also higher.

DETAILED DESCRIPTION

Referring more specifically to the pomological details of this new and distinct variety of white nectarine tree, the following has been observed during the third fruiting season under the ecological conditions prevailing at the orchards located near the town of Elne, in the Pyrénées-Orientales department, France. All observations have been made on rootstock cultivar. The rootstock was a 'INRA GF677' tree. All major color code designations are by reference to The R.H.S. Colour Chart (Fourth Edition) provided by The Royal Horticultural Society of Great Britain.

Tree:

*Size.*—Medium to high as compared to other common commercial nectarine cultivars. The tree size the first year was approximately 2.50 meters. The tree was pruned during each following dormant season to a height of approximately 2.50 meters. Current seasons shoots growth could reach 0.80 meters. So the tree size from the second year (second and next years) reached a final height of 3.30 meters including current seasons shoots length.

*Spread.*—Approximately 1.0 meter. The whole orchard was oriented to a central leader organization, with tree lines spaced of 4.0 meters and trees spaced of 1.0 meter in a same tree line.

*Vigor.*—Strongly vigorous. The present variety grew from about 60.0 centimeters to 80.0 centimeters in height during the first and following growing seasons. For second and following seasons, the variety was pruned to an approximate height of 2.50 meters.

*Productivity.*—Very productive. Fruit set is spaced by thinning to develop the remaining fruit into the desired market sized fruit. The number of the fruit set varies with the prevailing climatic conditions and cultivar practices employed during the bloom period, and is therefore not distinctive of the present variety.

*Bearer.*—Considered very regular. A thinning of 1 fruit out of 3 was necessary for the tree valorization. Thinning may not be too important because of the high magnifying potential of the fruit.

*Form.*—Semi-spread to semi-upright naturally.

*Density.*—Considered medium dense to dense.

*Hardiness.*—The present tree was grown and evaluated in France. The variety appears to be hardy under typical central Pyrénées-Orientales department climatic conditions. Fruits remain very attractive because they are well colored with an excellent semi-sweet flavor. Experimentations on different sites with winter chilling requirement comprised between 350 hours and 1200 hours showed a good behavior of the tree in all cases. No damages were caused by ascertained temperatures as low as −12° degrees Celsius. The tree was also very resistant to frosty springtime weather.

Trunk:

*Diameter.*—Approximately between 4.7 centimeters and 7.0 centimeters when measured at a distance of approximately 30.0 centimeters above the soil, on trees from the third growing season.

*Bark texture.*—Rough, with lenticels.

*Lenticels.*—Numerous lenticels are present on trees from the third growing season. The number of lenticels reaches 4 to 5 lenticels per $cm^2$. The lenticels range in size from approximately 0.15 centimeters in height and about 0.4 to 0.6 centimeters in width.

*Lentical color.*—The outside surface of lenticels has a silver-grey color (RHS GREY 201 C to 201 D), whereas the inside surface is brown (RHS GREYED ORANGE 166 C to 166 D).

*Bark coloration.*—The bark has a silver-grey color a little more pronounced than lenticels outside color (RHS GREY 201 A or RHS BLACK N200C).

Branches:

*Size.*—Mature branches and current season shoots are considered medium to thick for the variety. Mature branches show a length between 60.0 and 90.0 centimeters.

*Diameter.*—Average as compared to other nectarine varieties. The current season shoots have a diameter from 4.0 to 6.0 millimeters, and branches of trees from the third growing season have a diameter comprised between 10.0 and 16.0 millimeters.

*Current season shoots surface texture.*—Average, wood that is several years old has no furrowed appearance.

*Crotch angles.*—Primary branches are considered variable, but the crotch angles are generally between 50 degrees and 60 degrees from the horizontal axis. This particular characteristic is not considered distinctive of the variety, however.

*Internode length.*—Generally 25.0 millimeters to 35.0 millimeters.

*Color of mature branches.*—Brown (RHS GREY BROWN 199 A or GREYED GREEN GROUP 197 A to 197 B).

*Color of current season shoots.*—The color of new shoot tips is considered a light yellow green (RHS YELLOW GREEN 144 A to 144 C) on lower part of new shoot tips, whereas the upper part is colored brown-purple to brown-red (RHS GREYED PURPLE GROUP 187 A or GREYED RED 182 A) following the position on the shoot.

Leaves:

*Size.*—Considered medium to large for the species. Leaf measurements have been taken from vigorous, upright, current-season growth at approximately mid-shoot. The ratio leaf length/leaf width is above 3.42.

*Leaf length.*—From 142.0 to 165.0 millimeters with leaf petiole. Average length of 156.0 millimeters.

*Leaf width.*—From 38.0 to 56.0 millimeters. Average width of 45.0 millimeters.

*Leaf base shape.*—Concave relative to the leaf longitudinal axis.

*Leaf form.*—Lanceolate.

*Tip form.*—Acuminate, small.

*Leaf color.*—Upper leaf surface. Dark green (RHS GREEN 137 A). Lower surface. Of a lighter green (RHS GREEN 137 B to 137 C) than the upper leaf surface color. Leaf texture. Smooth. Leaf venation. Pinnately veined.

*Mid-vein.*—Color. Light green with a yellow touch (RHS YELLOW GREEN 145 D) and evolves with maturity. Leaf margins. Slightly undulating. Form. Considered slightly dentate. Uniformity. Leaves are isolated or grouped by 2 or 3. In this last case, it is found one leaf of normal size with one or two smaller leaves (size-reduction of 50% and more).

*Leaf petioles.*—Size. Considered short to medium. Length. About 5.0 to 9.0 millimeters. Diameter. About 1.0 millimeter. Color. Light green on the upper surface (RHS YELLOW GREEN 137 D to 137 C) and light green (RHS YELLOW GREEN 145 C to 145 D) on the lower surface.

*Leaf glands.*—Size. Considered small to medium. Their length is about 1.0 millimeter. Their width is between 0.8 and 1.0 millimeter. Number. Generally 2 to 3. Type. Reniform. Color. On young leaves, leaf gland color is considered pale green (RHS YELLOW GREEN 145 B). On older leaves, leaf gland color turns to a dark brown (RHS GREY BROWN 199 A to 199 B). Margins. Smooth and regular.

*Leaf stipules.*—Generally. No leaf stipules were observed. But as seen in the characteristic relative to the leaves uniformity, it is possible to find leaves by groups of 2 or 3, with a normal-size leaf and smaller ones.

Flowers:

*Flower buds.*—Generally. At pre-floral stage of development, the floral buds are conic in form with a round tip. Their form is evolving until blooming, with variable dimensions. Just before blooming, floral buds are approximately 10.0 millimeters wide and approximately 18.0 millimeters long. Color. This characteristic is dependent upon the proximity to bloom. At pre-floral stage of development, the bottom of the flowers buds, or calyx formed by sepals, is of purple-brown color (RHS GREYED PURPLE 183 A to 183 D or GREYED BROWN GROUP 199 A); the corolla formed by petals, is generally of pale pink color (RHS RED PURPLE 65 A to 65 C). Petals color shows an evolution until the end of blooming. Hardiness. The buds are considered hardy under typical central Pyrénées-Orientales department climatic conditions. No winter injury was noted during the last several years of evaluation in the central Pyrénées-Orientales department, with winter temperatures as low as −10° C. in January. The current variety has not been intentionally subjected to drought or heat stress, but the variety showed a very good resistance in orchard to temperatures up to 42° C. with an average temperature between 28° C. and 30° C. during 3 weeks in summer. Date of bloom. Generally late February. The first bloom was observed on Feb. 28, 2005. Second, third and fourth blooms took place respectively on Feb. 21, 2008, Mar. 1, 2009 and Mar. 16, 2010. Blooming time. Considered semi-early to semi-late in relative comparison to other commercial nectarine cultivars grown in the Pyrénées-Orientales department, France. The date of full bloom is observed at the middle of the blooming period. The date of bloom varies slightly with climatic conditions and cultural practices. Duration of bloom. Approximately 7 to 9 days. This characteristic varies slightly with the prevailing climatic conditions. Flower type. The variety is considered to have a showy type flower. Flower size. Considered medium. Flower diameter at full bloom is approximately 30.0 to 36.0 millimeters. Bloom quantity. Considered abundant, approximately 45 flowers per meter. Flower bud frequency. Generally 2 flower buds appear per node, occasionally 1.

*Petal.*—Size. Considered medium for the species. Length. Generally about 18.0 to 19.0 millimeters. Width. Generally about 18.0 to 19.0 millimeters. Petal form. Round. Petal count. Nearly always 5. Petal texture. Smooth and soft. Petal color. Both surfaces of the petal are colored with a medium pink (RHS RED PURPLE 65 A to 65 D) when young, darkening with advancing senescence. Fragrance. Soft.

*Petal claw.*—Form. The claw is considered to have a conic form with a slightly rounded tip. Length. Approximately 5.0 millimeters. Width. Approximately 3.0 millimeters. Petal margins. Slightly wavy, sinuate.

*Petal apex.*—Generally. The petal apices have a broad dome shape.

*Flower pedicel*.—Length. Considered medium to long and having an average length of approximately 3.0 to 5.0 millimeters. Diameter. Average 2.0 millimeters. Color. Brown to light brown (RHS GREY BROWN N199 C to N199 D).

*Calyx*.—Internal surface texture. Smooth and glabrous. Color. The outer surface of the calyx is considered purple-brown (RHS GREYED PURPLE 183 A to 183 D or GREY BROWN 199 A) color. The inner surface is washed-green yellow (RHS YELLOW 13 A to 13 B or YELLOW GREEN 150 A to 150 B).

*Sepals*.—Number. Generally 5. Surface texture. The outer surface has a fine pubescent texture. Size. Medium. Ovoid shape. Length. Approximately between 5.0 and 6.0 millimeters. Width. Approximately between 4.0 and 5.0 millimeters. Color. A flat red (RHS GREYED PURPLE 183 A to 183 D or GREY BROWN 199 A). Average number of stamens per flower. Average 40 stamens per flower.

*Anthers*.—Length. Medium. Color. Yellow orange red color (RHS YELLOW ORANGE 16 A to 16 D). Anthers are becoming brown (RHS GREYED PURPLE 178 A) when maturity is passed. The color evolves with flowering. Pollen production. Pollen is abundant, and has a yellow color (RHS YELLOW ORANGE 17 B to 17 C) evolving with the flowers maturity. The present variety is auto-fertile (self-pollinating).

*Filaments*.—Size. Variable in length, approximately 10.0 to 15.0 millimeters in length. Color. Considered pale pink (RHS RED PURPLE 62 C to 62 D or RED PURPLE 73 A to 73 B). The color is evolving with flowering.

*Pistil*.—Number. Usually 1. Length. Approximately from 14.0 to 18.0 millimeters including the ovary. Color. Considered very pale green (RHS YELLOW GREEN 150 D or RHS YELLOW GREEN 151 D). The color is evolving with flowering. Surface texture. Glabrous.

Fruits:

*Maturity*.—Very firm at maturity (shipping ripe).

*Date of first picking*.—Aug. 22, 2010, exceptionally late due to climatic conditions in winter 2010.

*Date of last picking*.—Sep. 4, 2010, exceptionally late due to climatic conditions in winter 2010. The date of harvest varies slightly with the prevailing climatic conditions.

*Size*.—Generally. Considered large, with a homogeneous size between them. Average cheek diameter. From 69.0 to 75.0 millimeters to 85.0 millimeters. Average axial diameter. From 63.0 millimeters 70.0 millimeters. Typical weight. Generally between 230.0 grams and 280.0 grams. This characteristic is highly dependent upon the prevailing cultural practices, and therefore is not particularly distinctive of the variety.

*Fruit form*.—Generally. Round to slightly oblong. The fruit is generally uniform in symmetry, viewed from pistil end. Fruit suture. Very shallow, extending from the base to the apex. No apparent callousing or stitching exists along the suture line.

*Suture*.—Color. This has generally a color similar to the blush fruit color, a bright red (RHS RED PURPLE 59 A to 59 B) on a ground (RHS RED 47 B to 47 D).

*Ventral surface*.—Form. Smooth. Apex. Not prominent, sometimes very slightly marked, very small. Base. Semi-flared, shallow. Stem cavity. Average depth of the stem cavity is about 8.0 to 9.0 millimeters. Average width is about 16.0 to 18.0 millimeters.

*Fruit skin*.—Thickness. Considered very thick and strong, and tenacious to the flesh depending on stage of maturity. Texture. Smooth. Taste. Semi-sweet, sugared, aromatic. Tendency to crack. None.

*Color*.—Blush color. This blush color is a homogenous bright red (RHS RED PURPLE 59 A to 59 B). The red blush covers 60% to 80% of the fruit skin surface. The percentage of the blush on the fruit skin surface can vary, and is generally dependant upon the prevailing conditions under which the fruit was grown. Ground color. The ground color appears until 20% to 35% of the fruit skin surface, and is considered washed-pink red (RHS RED 47 B to 47 D). Sometimes slightly light green on the peduncle side on a very small surface of 2% to 5% (RHS YELLOW GREEN 145 C to 145 D). Fruit stem. Medium in length, approximately 7.0 to 8.0 millimeters. Diameter. Approximately 4.0 to 5.0 millimeters. Color. Pale green (RHS YELLOW GREEN 145 A to 145 B).

*Flesh*.—Ripens. Very homogenous, slow, very evenly. Texture. Very firm, very dense, crunchy, luscious, and juicy at harvesting maturity stage. Fibers. Not fibrous. Aroma. Pronounced. Eating quality. Considered very good, aromatic. Flavor. Considered semi-sweet. The Brix is generally superior 13 degrees and acidity is comprised between 6 and 9 meq/100 ml. The flavor is considered juicy and aromatic. Juice. Very juicy at complete maturity. Brix. Superior to 13.0 degrees. This characteristic varies slightly with the number of fruit per tree; prevailing cultural practices; and the surrounding climatic conditions. Flesh color. White flesh (RHS WHITE 155 A to 155 B) with a slight red pigmentation in the stone cavity and star-shaped around the stone cavity (RHS RED 53 A) on approximately 7 millimeters.

*Stone*.—Type. Clingstone. The level of adherence evolves with the stage of maturity of the fruit. Stone cavity. Medium to large size, with an ovoid form and dimensions corresponding to the stone's dimensions. Size. Considered medium to large for the variety. The stone size varies significantly depending upon the tree vigor, crop load and prevailing growing conditions. Length. Approximately 35.0 millimeters. Width. Approximately 22.0 millimeters. Diameter. Approximately 19.0 millimeters. Form. Elliptic. Base. Straight to slightly oblique.

*Apex*.—Shape. The stone apex is prominent.

*Stone surface*.—Surface texture. Usually the pit is transversely furrowed on its entire surface. Furrows are more pronounced toward the apex. The stone is pitted toward the base. Relief is prominent generally and present basally. Ridges. The surface texture is generally characterized by more prominent ridges along the ventral edges and is more prominent at the apical tip.

*Ventral edge*.—Width. Considered small to medium, and having a dimension of approximately 2.0 millimeters at mid-suture.

*Dorsal edge*.—Shape. Grooved. Stone color. The color of the dry stone is purple brown (RHS GREYED PURPLE N186C or 187 A to 187 B) with some zones of light brown (RHS GREYED ORANGE 173 C to 173 D). Tendency to split. Splitting is absent or very low, depending on climatic conditions between blooming period and stone hardening.

*Kernel*.—Size. Medium. Length. About 19.0 millimeters. Width. About 12.0 millimeters. Thickness. About 5.0 millimeters. Form. Considered oblate and elliptic. Pellicle. Slight pubescent. Color. The kernel skin is orange brown (RHS GREYED ORANGE N167 A or 167 A to 167 B). The almond, which is the seed of the kernel, is cream-white (RHS WHITE 155 B). The kernel and its embryo are mature at the time of fruit maturity.

*Use*.—The subject variety 'NECTARBONDANT' is considered to be a white nectarine tree of the semi-late season of maturity, and which produces fruits that are considered large, firm, and attractively colored. Fruits are excellent for uncooked consumption, crunchy or at full maturity. Due to their flesh quality, firmness and density, they can also be commercialized as $4^{th}$ range product (packed fruit or fruit in bags for example). And they are also useful for both local and very long distance shipping.

*Keeping quality*.—Excellent. Fruit stayed a little more than one week on tree before harvest and then, has stored well more than 4 weeks after harvest at 2.0 degree Celsius. They have a slow maturation and a long shelf life both on the tree after growth completion and after harvesting without alteration.

*Shipping quality*.—Considered very good. The fruit of the new nectarine variety showed minimal bruising of the flesh or skin damage after being subjected to normal harvesting and packing procedures. Its resistance to handling during harvest and packing and its long shelf life without alteration after harvest easily permit 3 weeks-shipping at 2° degree Celsius.

*Resistance to insects and disease*.—No particular susceptibilities were noted. The present variety is low sensitive to powdery mildew, and low sensitive to conservation diseases and decay due to its thick and strong skin.

Although the new variety of nectarine tree possesses the described characteristics when grown under the ecological conditions prevailing near Elne, Pyrénées-Orientales department, France, it should be understood that variations of the usual magnitude and characteristics incident to changes in growing conditions, fertilization, pruning, pest control and horticultural management are to be expected.

We claim:

1. A new and distinct variety of white nectarine tree as illustrated and described, characterized by a large fruit of very long shelf life without alteration after harvesting, and with a semi-sweet white flesh of high eating quality and an attractive skin color, with a very high percentage of bright red.

* * * * *